United States Patent [19]

Ideker et al.

[11] Patent Number: 5,540,723
[45] Date of Patent: Jul. 30, 1996

[54] METHOD AND APPARATUS FOR DELIVERING AN OPTIMUM SHOCK DURATION IN TREATING CARDIAC ARRHYTHMIAS

[75] Inventors: Raymond E. Ideker; Gregory P. Walcott, both of Durham, N.C.; Stephen J. Hahn, Roseville, Minn.

[73] Assignees: Duke University, Durham, N.C.; Cardiac Pacemakers, Inc., St. Paul, Minn.

[21] Appl. No.: 132,373

[22] Filed: Oct. 6, 1993

[51] Int. Cl.⁶ .................................................. A61N 1/39
[52] U.S. Cl. .................................................. 607/7
[58] Field of Search ........................ 607/5, 7, 8, 11

[56] References Cited

U.S. PATENT DOCUMENTS

| | | |
|---|---|---|
| 4,821,723 | 4/1989 | Baker, Jr. et al. . |
| 5,179,946 | 1/1993 | Weiss . |
| 5,222,501 | 6/1993 | Ideker et al. . |
| 5,224,476 | 7/1993 | Ideker et al. . |
| 5,230,336 | 7/1993 | Fain et al. ................................. 607/7 |
| 5,385,575 | 1/1995 | Adams ...................................... 607/5 |

OTHER PUBLICATIONS

S. A. Feeser, et al. *Strength–Duration and Probability of Success Curves for Defibrillation with Biphasic Waveforms Circulation* 82, pp. 2128–2141 (1990).

M. W. Kroll, *A Minimal Model of the Monophasic Defibrillation Pulse PACE* 16 pp. 769–777 (1993).

*Primary Examiner*—William E. Kamm
*Assistant Examiner*—Scott M. Getzow
*Attorney, Agent, or Firm*—Bell, Seltzer, Park & Gibson

[57] ABSTRACT

The present invention provides apparatus and methods for delivering an optimum electrical shock in treating cardiac arrhythmias. The invention comprises apparatus for producing an electrical waveform signal at least at two electrodes. The voltage or current of the signal is then detected to determine the signal time constant. The signal time constant is then used in conjunction with a model time constant to determine when the peak amplitude is reached. The waveform is then interrupted when the peak amplitude is reached. Also provided are methods of selecting a cardiac defibrillator by measuring the impedance of implanted electrodes and then selecting a defibrillator having a capacitor which provides an RC time constant equal to that of a model time constant.

28 Claims, 4 Drawing Sheets

METHOD AND APPARATUS FOR DELIVERING AN OPTIMUM SHOCK DURATION IN TREATING CARDIAC ARRHYTHMIAS

This invention was made with Government support under grant number HL44066 from the National Institutes of Health. The Government has certain rights to this invention.

FIELD OF THE INVENTION

The invention relates to the field of treatment for cardiac arrhythmias, and more particularly to methods and apparatus for delivering the optimum duration of an electrical shock to the heart during treatment of cardiac arrhythmias.

BACKGROUND OF THE INVENTION

Ventricular fibrillation, an often fatal heart arrhythmia, can be terminated by the application of one or more electrical current pulses delivered to the heart through electrodes applied to the chest or implanted within the body. Since the first use on humans of a completely implantable cardiac defibrillator in 1980, research has focussed on making continually smaller and more efficient defibrillation devices. In addition, reducing the defibrillation threshold (DFT) energy level applied to the heart by the defibrillation pulses reduces the likelihood of damaging tissue adjacent the electrodes.

A conventional implantable defibrillator includes an electrical pulse generator and an arrhythmia detection circuit coupled to the heart by a series of two or more electrodes implanted in the body. A battery power supply, and one or more charge storage capacitors are used for delivering defibrillation shocks in the form of electrical current pulses to the heart.

Currently, the primary constraint in reducing the size of an implantable defibrillator is reducing the battery size and the size of the storage capacitor(s). Accordingly, improvements in the area of implantable defibrillators have focussed in two areas: (1) more efficient defibrillation waveforms, and (2) more efficient electrode configurations and placements. Stated in other words, the primary variables that can be adjusted in the design to lower the shock strength required for defibrillation include those variables relating to the defibrillation waveform, such as duration, polarity, and waveshape, and those variables relating to the electrodes, such as materials, size, shape, and location.

An example of a development in the area of electrodes is U.S. Pat. No. 4,827,932 to Ideker et al. which relates to a pair of spaced apart epicardial implantable defibrillation patch electrodes. A respective patch electrode is attached over each of the right and left ventricles in an attempt to achieve a uniform voltage gradient throughout the entire ventricular mass.

In the area of defibrillation waveforms, U.S. Pat. No. 4,641,656 to Smits discloses a method of applying a sequence of defibrillating pulses to the heart from a series of four electrodes. Two adjacent electrodes have positive polarity and the other two electrodes have negative polarity in an attempt to concentrate defibrillation energy in the heart wall rather than through the center of the heart. Two or more such pulses are applied, with a reverse in polarity of one pair of opposing electrodes between each pulse. Another pulsing scheme is disclosed wherein the polarity of the four electrodes alternates with each adjacent electrode, and with all four electrodes used simultaneously to defibrillate the heart.

Other examples of defibrillating waveforms are disclosed in U.S. Pat. No. 4,637,397 to Jones et al., No. 4,800,883 to Winstrom, and No. 4,821,723 to Baker, Jr. et al. These patents disclose multiphasic defibrillation waveforms wherein the polarity of pulses is reversed. U.S. Pat. No. 4,768,512 to Imran relates to a high frequency truncated exponential waveform. U.S. Pat. No. 4,727,877 to Kallok discloses a transvenous lead configuration wherein a first electrical pulse is delivered to a first pair of electrodes between the right ventricular apex and the superior vena cava, and after a predetermined delay, a second pulse is delivered to a second pair of electrodes between the right ventricular apex and the coronary sinus.

None of these efforts, however, sufficiently control the waveform to maximize the efficiency of the defibrillation pulses and thereby reduce the risk of damage to adjacent tissue and minimize the size of batteries, capacitors and other defibrillator hardware.

SUMMARY OF THE INVENTION

It is therefore, one object of the present invention to provide a method and apparatus for producing an optimum waveform for treating cardiac arrhythmias of a subject. It is a further object that the defibrillator provide an optimum monophasic or biphasic waveform for defibrillating the heart of a subject.

An additional object of the present invention is to provide an apparatus with optimal capacitance for producing waveforms which produce an electric counter-shock pulse for treating cardiac arrythmia of the heart of a subject and methods of selecting such an apparatus to thereby reduce the size of the battery and capacitor required for such an apparatus. The present object additionally facilitates implanting such an apparatus in a subject.

A further object of the present invention is to provide a waveform which minimizes damage to the cardiac tissue of the area of the heart receiving the counter-shock waveform signal.

These objects and advantages are achieved by a first embodiment of an apparatus according to the present invention. The first embodiment being a cardiac electric counter-shock apparatus, comprising circuitry for delivering a waveform signal to a pair of electrodes. The apparatus further comprises circuitry to detect an electrical characteristic of a pair of electrodes during delivery of the waveform signal and for calculating a waveform time constant ($t_s$) from the detected electrical characteristic. The defibrillator stores a model time constant ($t_m$) and calculates when a peak membrane voltage is reached based on the waveform time constant and the model time constant. Finally, the apparatus comprises switching circuitry to interrupt the waveform signal when the peak membrane voltage is reached.

A further aspect of the first embodiment of the present invention optionally provides a biphasic cardiac defibrillation apparatus having circuitry for delivering a second waveform after the first waveform where the second waveform has a polarity opposite that of the first waveform. This biphasic apparatus may also detect an electrical characteristic of a pair of electrodes during delivery of the second waveform signal and determine a waveform time constant ($t_s$) from the electrical characteristic during the second waveform signal. The apparatus also calculates when the membrane baseline voltage is reached from the second waveform time constant and the model time constant and interrupts the second waveform signal when the membrane baseline voltage is reached.

A second embodiment of the present invention provides a cardiac arrythmia treatment method comprising delivering a waveform signal to a pair of electrodes when the electrodes are positioned for defibrillating the heart of a subject. An electrical characteristic of the pair of electrodes is detected during delivery of the truncated exponential waveform signal and a waveform time constant ($t_s$) is determined from the electrical characteristic. A model time constant ($t_m$) for a model response to the waveform is provided and the time when a peak membrane voltage is reached is determined from the waveform time constant and the model time constant. The waveform signal is then interrupted when the peak membrane voltage is reached.

A further aspect of the method comprises delivering a second truncated waveform signal of opposite polarity to the first waveform signal to the pair of electrodes. Optionally, an electrical characteristic of the pair of electrodes is detected during delivery of the second waveform signal and determines a waveform time constant ($t_s$) from the electrical characteristic during the second waveform signal. The time when the membrane baseline voltage is reached is then calculated from the second waveform time constant and the model time constant. The second waveform signal is then interrupted when the membrane baseline voltage is reached.

A third embodiment of the present invention provides a method of selecting a cardiac arrythmia treatment apparatus for implantation in a subject. The selection method comprises providing a set of implantable cardiac arrythmia treatment apparatus which deliver a waveform signal, each member of the set having a different value of storage capacitor for delivering the waveform signal. A pair of electrodes are implanted in a subject, with the electrodes positioned for providing an electric counter-shock to the heart of the subject. The impedance across the pair of electrodes is measured after implantation. The cardiac arrythmia treatment apparatus is then selected from the set of apparatus based on the impedance and the storage capacitance of the apparatus. The selected apparatus is then implanted in the subject.

A fourth embodiment of the present invention is a set of implantable cardiac arrythmia treatment apparatus which deliver a waveform signal, each member of the set having a storage capacitor for delivering the waveform signal, and wherein each member of the set has a storage capacitor with a fixed capacitance different from the other members of the set.

DETAILED DESCRIPTION OF THE INVENTION

Figure 1:
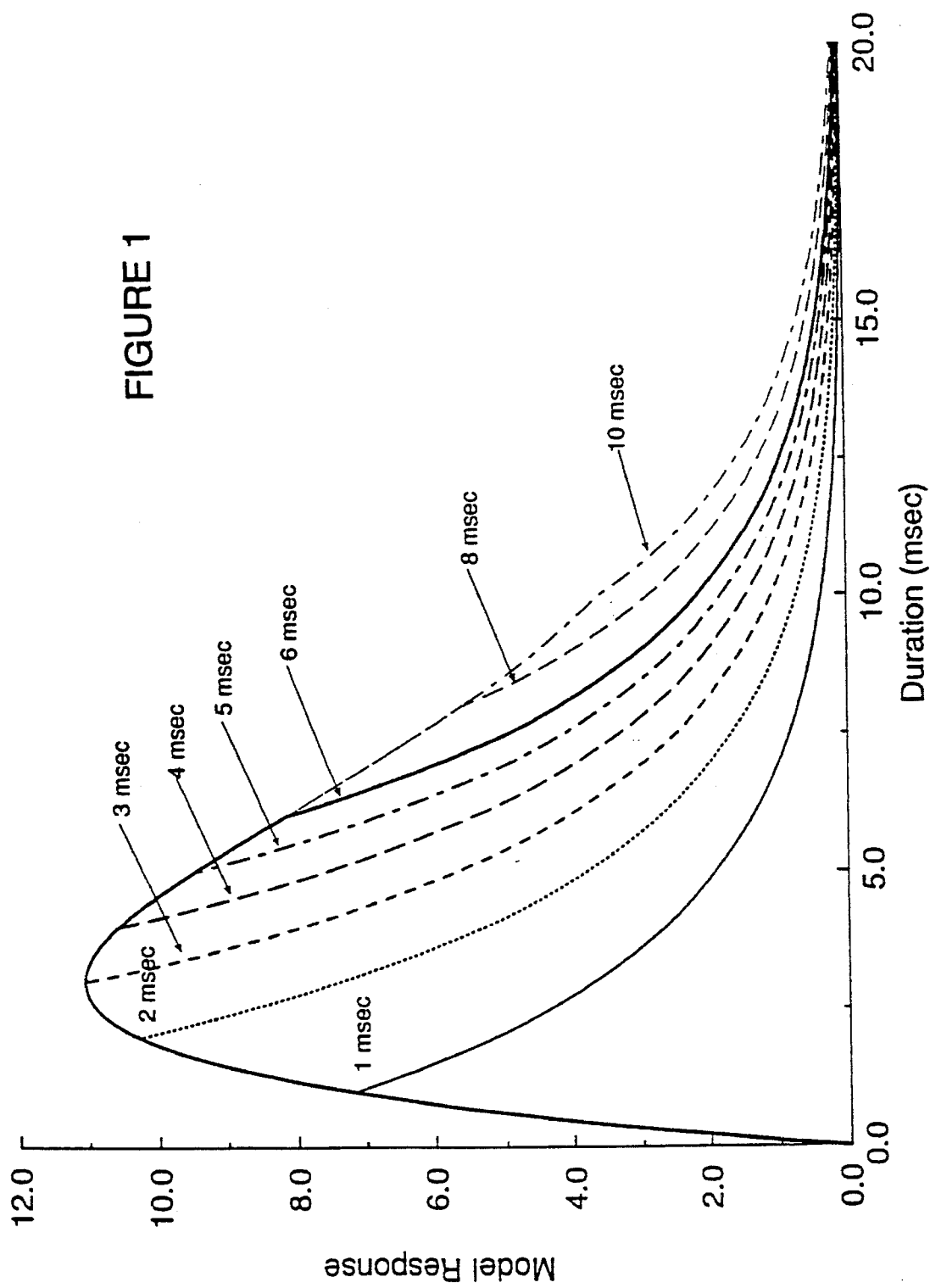
FIG. 1 is a graph of the model response to a monophasic truncated exponential waveform with varying pulse durations.

The present invention will now be described more fully hereinafter with reference to the accompanying drawings, in which preferred embodiments of the invention are shown. This invention, however, may be embodied in many different forms and should not be construed as limited to the embodiments set forth herein. Rather, applicants provide these embodiments so that this disclosure will be thorough and complete and will fully convey the scope of the invention to those of skill in this art.

The methods and apparatus as described below are described with reference to a cardiac defibrillator. However, as will be appreciated by one of skill in this art, these methods may be readily extended to any apparatus which treats arrhythmias with electric counter-shock. For example, the principles of the present invention apply equally well to the treatment of atrial tachyarrhythmias, atrial fibrillation, reentrant tachyarrhythmias, ventricular tachycardia, as well as ventricular fibrillation. These principles aid in any device which delivers an electric pulse to the heart to treat a cardiac arrythmia.

The membrane of the cardiac myocyte serves as both a resister and a capacitor to current flow. Cardiac activation and, perhaps, defibrillation, is thought to occur when an electrical stimulus changes the transmembrane potential by at least a certain minimum amount to raise the transmembrane potential above a particular threshold value. This threshold transmembrane potential may need only be reached for an infinitesimal small interval of time, however, the principles of the present invention can easily be extended if the threshold potential must be exceeded for a certain minimum period of time to cause stimulation or defibrillation. The description provided below is for providing a waveform which reaches the desired threshold voltage and then immediately begins to return to the baseline voltage. As will be appreciated by one of skill in this art, the principles of the present invention may be readily extended to provide a waveform signal which maintains a voltage above the desired threshold voltage for a selected finite time by increasing the duration of the stimulating pulse.

The resistance and capacitance of the membrane of the cardiac myocyte form an RC network. This means that an applied voltage across the membrane does not appear immediately when the voltage is applied, but increases as one minus an exponential function as the capacitor is charged. Once this time constant is known, the time after the start of the shock at which the change in transmembrane potential reaches a peak value can be calculated for any shock waveform. This technique can be used to determine the waveform that can stimulate and/or defibrillate with the smallest peak voltage or total energy. As an alternative to creating the optimum waveform, this technique can be used to produce the best waveform from those that can be practically delivered by a defibrillator. For example, internal defibrillators deliver a truncated exponential waveform by charging a capacitor within a defibrillator to a predetermined voltage and then discharging this capacitor through the defibrillator electrodes for a certain amount of time. The capacitor is then disconnected from the defibrillation electrodes, truncating the exponentially decaying shock waveform.

Excitable media in general and the heart in specific, has traditionally been modelled as a parallel RC circuit. If a square wave is used as input to the model, the resulting relationship is the Lapique equation for stimulation.

$$V(t) = at_m/C_m(1-e^{t/t_m})$$

where V(t) is the voltage across the model at time t, a is the amplitude of the input square wave in amps, $t_m$ is the model time constant, and $c_m$ is the value of the capacitor in the model.

This model may be extended to predict V(t) when any shape waveform are used as input. The threshold duration relationship for an input waveform may be derived by convolving the impulse response of a parallel RC circuit with the input waveform. The derivative of the result of the convolution is then taken and set to 0 to solve for the peak response time.

The above procedure was utilized for truncated exponential waveforms are used as input. The equation for the response of a parallel RC circuit to a decaying truncated exponential waveform is:

$$V(t) = \frac{a t_s t_m (e^{t/t_s} - e^{t/t_m})}{c_m (t_s - t_m)}$$

where $t_s$ is the waveform time constant.

This equation can be applied to defibrillation. If all the tissue that is between the two electrodes is represented as a parallel RC circuit, then a defibrillation threshold can be defined as that input to the model that raises the model response V(t) to some fixed response.

While $C_m$ is unknown it is only a scaling factor and, therefore, does not impact the remainder of the analysis. In addition, $t_m$ is also unknown. From analysis of the Lapique equation above, it can be shown that: $t_m = 0.693 \, t_c$ where $t_c$ is the chronaxie time. Based upon the reported values for chronaxie from the literature from defibrillation of 1 msec to 4 msec, then a range of $t_m$ values of from about 1.5 to about 4.5 msec results. Other methods of determining $t_m$ include transmembrane tissue studies using a double barrelled microelectrode in a tissue bath. Tissue studies in animals may be analogized to the human heart.

While $t_m$ varies from subject to subject, for purposes of the present example, $t_m$ may be approximated as 3 msec. From these equations, the optimal capacitor for the exponential waveform can be determined. To maximize V(t) for a given input, then $t_s$ should be set equal to $t_m$. Furthermore, $t_s$ is simply RC, the impedance between the two electrodes multiplied by the capacitance value of the waveform. Human impedances vary from about 20Ω to about 80Ω with a mean of 40Ω. Therefore, for purposes of the present example, using the mean of 40Ω results in the optimal capacitor value for the exponential waveform of 75 μf. Thus, the optimum capacitance for a defibrillator may be selected by measuring the resistance of the implanted electrodes and then selecting a capacitor which makes the RC time constant of the defibrillator equal to the model time constant.

Alternatively, in an internal defibrillator the capacitance and shock duration can be calculated to minimize either the voltage to which the capacitor must be charged or the total energy to which the capacitor is charged based on the RC time constant of the cardiac membrane. A mean value of this model time constant $t_m$ can be determined experimentally either by determining the strength-duration relationship for defibrillation directly in humans or, by extrapolation to humans from animals. Furthermore, as will be understood by one of skill in this art, $t_m$ may be determined for a particular subject from a strength duration analysis of the subject where the strength duration curve is defined as an exponential with $t_m$ as the time constant of that function.

Capacitor discharge waveforms are truncated in order to improve defibrillation efficacy. Analysis of the above equations show that the model response reaches a maximum response at some time t and then slowly decays back towards zero. If the truncated time is longer than this time t, then the energy delivered after time t is wasted since is does not lead to any increase in V(t). This time t is $(\log(t_m/t_s)/(1/t_s - 1/t_m))$. Note that this equation varies time t as a function to $t_s$. The capacitor in an implantable device is fixed, but the impedance across the electrodes can vary from patient to patient, and over time in the same patient. Since patient impedance can be determined as a shock is being delivered, the optimal pulse duration can be determined for each shock and the pulse truncated after that duration. The capacitance of the treatment apparatus described herein are discussed with reference to a capacitor value in the device. However, as will be readily appreciated, the capacitance of the device or apparatus need not come from a single passive capacitor but may be an effective capacitance of the device with contributions from a variety of sources.

In addition to the above application with respect to monophasic truncated exponential waveforms, these principles may be applied to biphasic truncated exponential waveforms as well. As with the monophasic waveform application, the pulse duration of a first truncated exponential waveform for a particular subject is determined by measuring the voltage at the electrodes and determining $t_s$ for the first pulse of a first polarity. The duration of the pulse is then determined as described above and the pulse truncated when that duration is reached. In the biphasic application the second pulse is then applied after the first pulse. This second pulse is of opposite polarity to the first pulse and is truncated when the potential of the membrane is restored to the initial voltage before the first pulse is applied. This initial voltage may be referred to as a baseline voltage and may be 0 volts or may be the resting voltage of the heart. The duration of the second pulse may be determined in a similar manner as the first pulse. Solving the above equations for the duration t which results in restoring the potential to the baseline voltage results in the following equation:

$$t = \frac{\log\left( e^{d1(\frac{1}{t_m} - \frac{1}{t_s})} - 1 + e^{\frac{d1}{t_s}} e^{d1(\frac{1}{t_m} - \frac{1}{t_s})} \right) + \frac{d1}{t_s}}{\frac{1}{t_m} - \frac{1}{t_s}}$$

where $t_m$ may be the same model time constant as used for the first pulse or may be unique to the second pulse and $t_s$ is determined for the second pulse from the impedance of the electrodes and heart and the values of the capacitance for the second pulse and d1 is the duration of the first pulse. Preferably the second pulse duration is not longer than 1.5 to 2 times the duration d1 of the first pulse. The second pulse may then be truncated at the appropriate time to efficiently return the membrane to the baseline voltage.

As seen in FIG. 1, the model response to a constant amplitude monophasic waveform varies as the duration of the pulse varies. In FIG. 1, the amplitude of the response initially increases with increased pulse duration but ultimately reaches a maximum and then begins to decay. Thus, in the response depicted in FIG. 1, the energy in the monophasic truncated exponential waveform after 3 milliseconds does not contribute to increased peak amplitude and is therefore inefficient.

Figure 2:
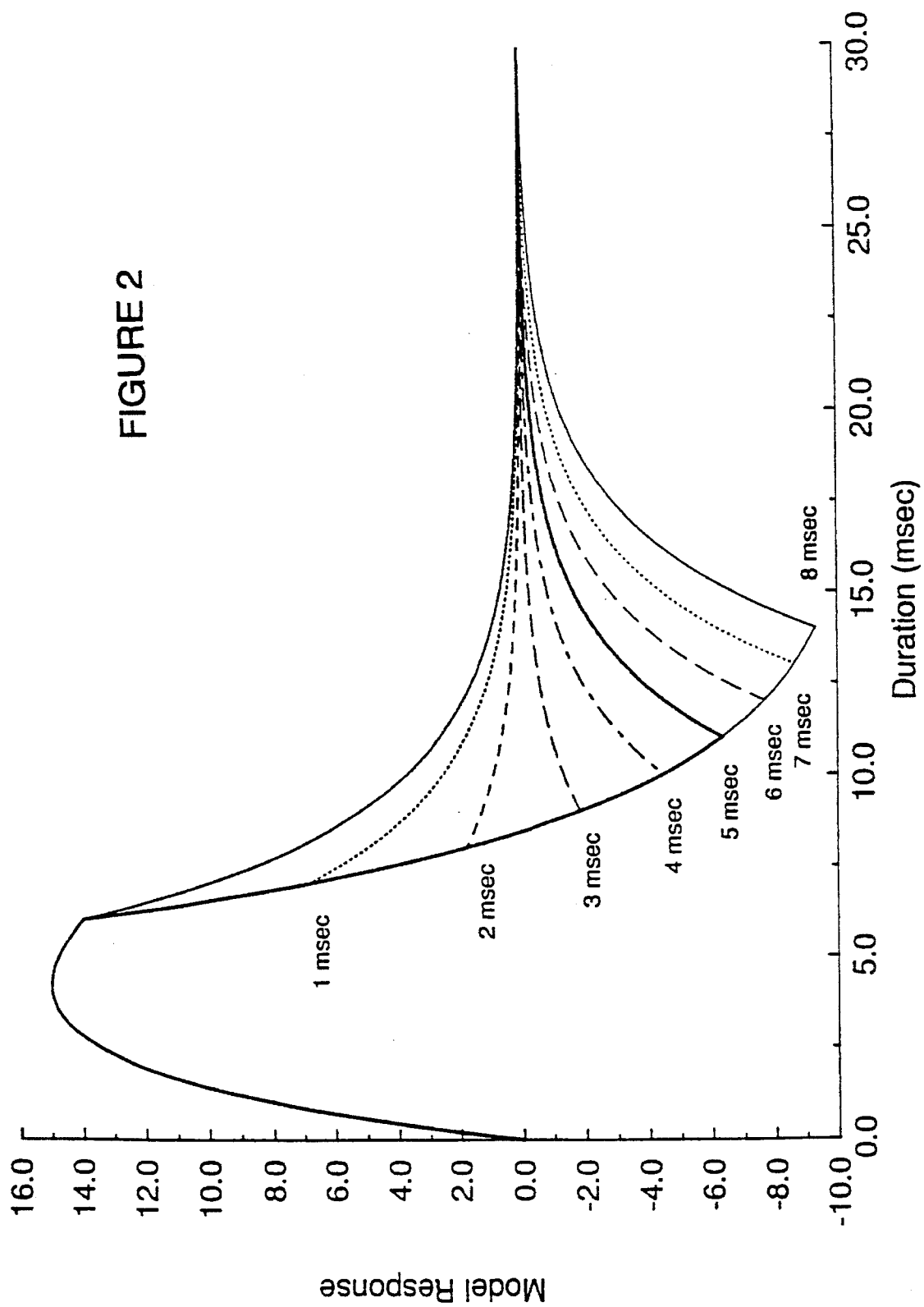
FIG. 2 is a graph of the model response to a biphasic truncated exponential waveform with varying second pulse durations.

FIG. 2 illustrates the model response to a biphasic waveform having a 6 millisecond first pulse of constant amplitude. The various dashed lines represent varying durations of the second pulse of biphasic waveform. The responses depicted in FIG. 2 illustrate that as the duration of the second pulse increases the energy of the second pulse causes the amplitude of the response to overshoot the baseline amplitude and is therefore inefficient.

Figure 3:
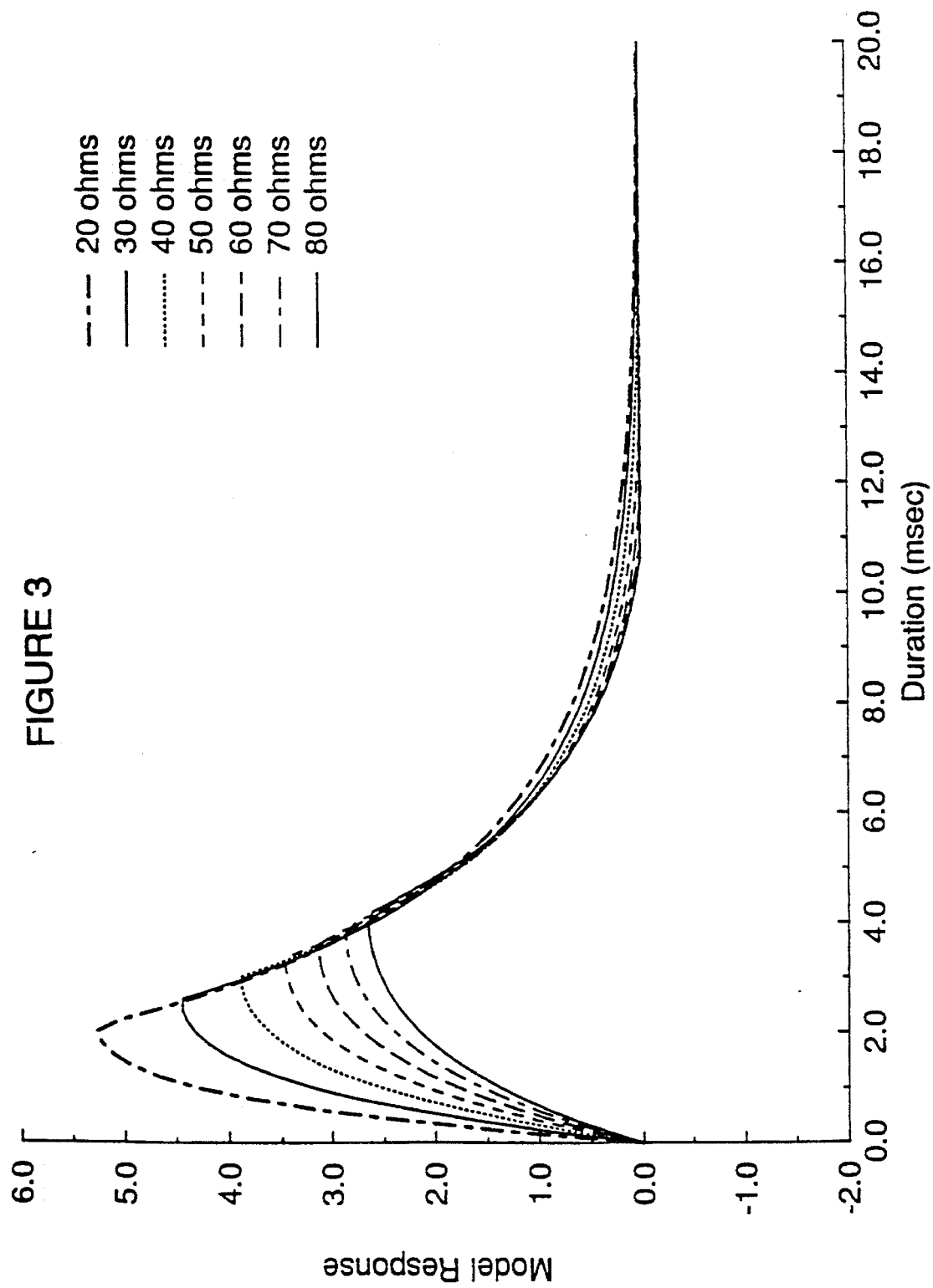
FIG. 3 is a graph of the model response to an optimal biphasic truncated exponential waveform according to the present invention.

As is seen in FIGS. 1 and 2, the duration of the first pulse and the duration of the second pulse dramatically impact the response waveform. FIG. 3 illustrates the optimized biphasic waveform according to the present invention for various electrode impedance values. As seen in FIG. 3, the peak response amplitude is achieved for each of the electrode impedances and the response returns to the baseline value without any overshoot.

While the present invention has been described with respect to the use of truncated exponential waveforms, the principles of the present invention apply equally well to other waveforms. The optimum duration of any waveform may be derived for both the initial pulse to reach a threshold voltage and for an opposite polarity pulse to return to the baseline voltage.

Particular embodiments of the present invention will now be described with reference to FIG. 4.

Figure 4:
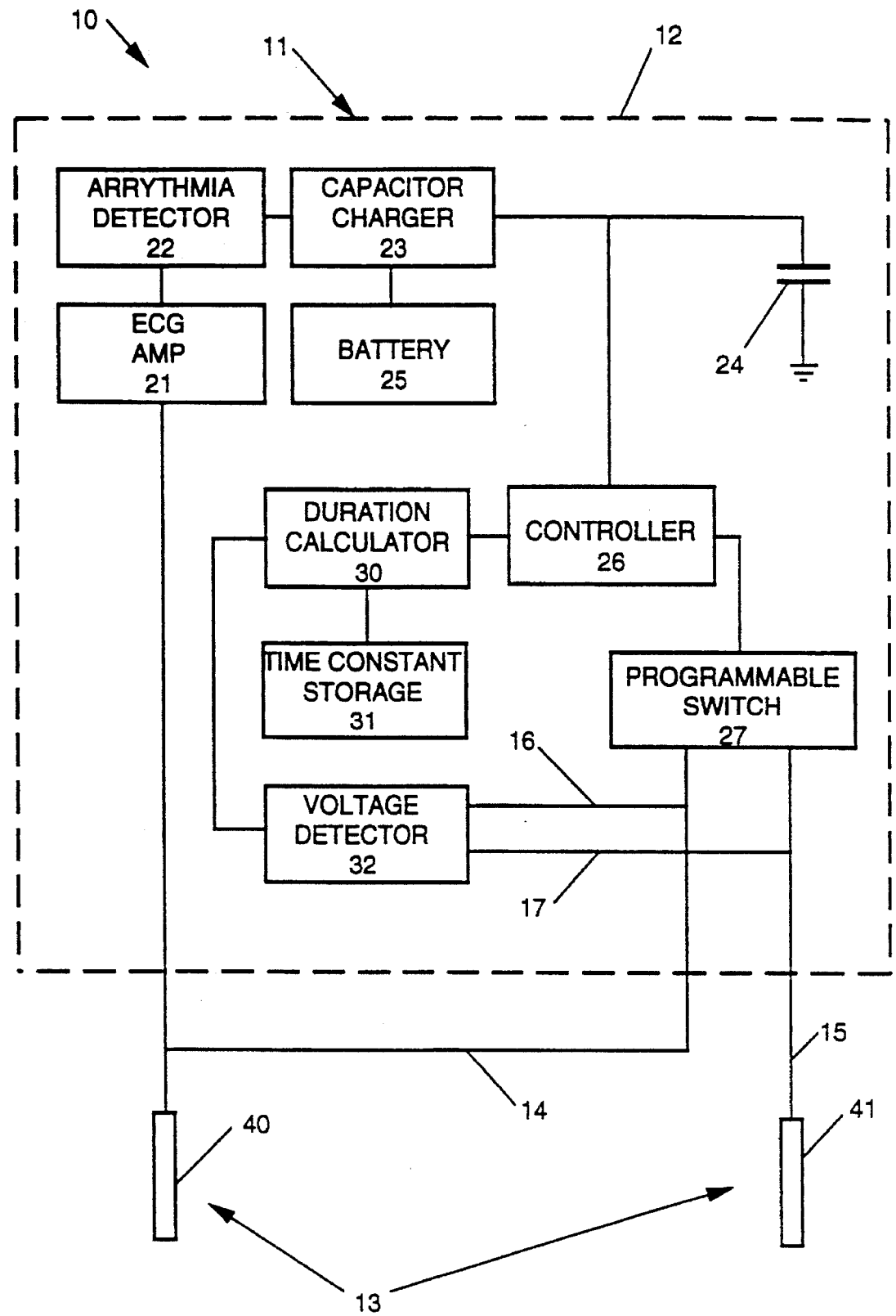
FIG. 4 is a schematic diagram illustrating a cardiac defibrillator according to the present invention.

As shown in the schematic diagram of FIG. 4, one embodiment of the present invention comprises an implantable apparatus 10 for controlling cardiac arrythmia. The apparatus according to the present invention includes an electronic circuit 11 contained within an implantable housing 12. The electronic circuit 11 is connected by a series of leads 14 and 15 to an electrode configuration 13 including a series of electrodes positioned adjacent portions of the heart.

The electronic circuit 11 includes a conventional ECG amplifier 21 for amplifying sensed cardiac signals. The amplified cardiac signals are analyzed by a conventional arrhythmia detector 22 which determines if and what type of arrhythmia is present. The arrhythmia detector 22 may be one of several types well known to those skilled in the art and is preferably capable of distinguishing between high rate malignant tachycardia and ventricular fibrillation so as to deliver lower energy shocks in the former case than those to be delivered in the latter case.

A capacitor charging circuit 23, in response to a signal from the arrhythmia detector 22, charges the storage capacitor 24 to a predetermined voltage from the battery 25. The voltage may be selected prior to implantation of the apparatus 10 or may be dependent on the determination of the arrhythmia detector 22. The discharge of the capacitor 24 is controlled by the controller 26, or multi-phasic circuit, such as described in U.S. Pat. No. 4,850,357. The capacitor 24 may be a single capacitor or a bank of parallel connected capacitors of equivalent capacity as would be readily understood by those skilled in the art.

The controller 26 delivers electrical pulses to the electrodes through a programmable switch 27. As would be readily understood by those skilled in the art, the voltage waveform delivered by the capacitor 24 may be a decaying exponential waveform. The capacitor charger 23, capacitor 24, battery 25, controller 26 and programmable switch 27 thus form an electrical pulse generator for the apparatus 10.

Upon the generation of a voltage pulse, voltage detector 32 monitors the voltage at electrodes 40 and 41 through leads 16 and 17. This voltage is provided to the duration calculator 30 for determination of the time constant $t_s$ for the pulse. The time constant is determined by measuring the voltage at the electrodes 40 and 41 and determining the rate of change of the voltage at the electrodes 40 and 41. It will be understood by one of skill in this art that from the rate of change of the voltage at the electrodes 40 and 41, the time constant $t_s$ may be readily determined. It will be further understood by one of skill in the art that, while the embodiment of the present invention illustrated in FIG. 4 utilizes voltage detection to determine the time constant $t_s$, alternatively the current through the electrodes 40 and 41 could be measured and the time constant $t_s$ determined from the current. One method of measuring the current would be to place a low value of resistance in series with the electrodes 40 and 41 and measure the voltage across that resistance. This voltage is then directly proportional to the current through the electrodes. Once the time constant $t_s$ is determined the duration calculator 30 uses $t_s$ combined with the appropriate model time constant from the time constant storage 31 to determine the appropriate duration of the pulse.

As would be understood by those having skill in the art, time constant storage 31 provides storage means for a plurality of time constants.

For a monophasic system the duration of the pulse is determined such that the pulse is terminated when maximum voltage at the tissue is reached. For a biphasic system the duration for maximum voltage is determined for the first pulse and the duration to return the tissue to the baseline voltage is determined for the second pulse of opposite polarity. The determination of the appropriate duration of the pulses may be carried out through the use of the principles described above.

The pulse duration information may then be transferred from the duration calculator 30 to the controller 26 which interrupts the pulse after the desired duration is reached by controlling programmable switch 27. As will be understood by one of skill in the art, the voltage detector 32, the duration calculator 30 and the time constant storage 31 may utilize electronic circuits known to one of skill in the art for measuring voltages, storing information and performing mathematical calculations. As will be further understood by one of skill in this art, the voltage detector 32, the duration calculator 30 and the time constant storage 31 may comprise a plurality of integrated circuits or may be incorporated into a single integrated circuit or may be incorporated into the electronic circuitry of the electric pulse generator described above.

With respect to the time constant storage 31 the values of the model time constant $t_m$ may be incorporated into the device at manufacture or may be programmed into the device at the time of implantation. Thus, the model time constant may be adjusted for each individual subject. Furthermore, the model time constant may be updated over time after implantation in a particular subject. The ability to update the model time constant after implantation would allow the device to compensate or adjust for variations over time of the subject's cardiac membrane RC time constant. Furthermore, one model time constant may be used for both monophasic and biphasic systems and for both pulses of biphasic systems or individual model time constants may be utilized for the first and second pulses of a biphasic system. In the present invention model time constants of from about 1 to about 4 milliseconds are preferred and from about 2.5 to about 3.5 milliseconds are more preferred.

A further aspect of the present invention involves placing the electrodes 40 and 41 in contact with the cardiac membrane of the subject. As will be appreciated by one of skill in this art, the number and location of the electrodes may be selected to increase the efficiency of the defibrillator. One such placement of the electrode is described in U.S. Pat. No. 5,224,476. After placing the electrodes 40 and 41 and the electrode leads 14 and 15 in the subject, the RC model time constant $t_m$ constant may be determined for the subject and the electrode placement by determining the strength-duration relationship for defibrillation. Various external apparatus known to one of skill in this art may be connected to leads 14 and 15 for determining the model time constant. After determining the time constant it would then be stored in the implantable electric circuitry 11 in the time constant storage 31. Leads 14 and 15 would then be connected to the electronics 11 and the device implanted in the subject.

The cardiac arrythmia apparatus described above has been described with respect to monophasic and biphasic truncated exponential waveforms. However, the benefits of the present invention may also be realized using other waveforms. Furthermore, the present invention has been described above with reference to producing a single shock pulse, however, as will be appreciated by one of skill in the art, the principles and methods of the present invention are equally applicable to multiple pulses or a series of pulses of varying or similar waveforms.

As will be understood by one of skill in this art, the benefits of the present invention may also be realized in a non-implantable, external defibrillator. Such a device would have essentially the same schematic representation as that shown in FIG. 4 but would not be restricted by the size limitations of the implantable device.

A second embodiment of the present invention is a method of defibrillating the heart of a subject. The method involves providing a truncated exponential waveform to a set of electrodes positioned so as to defibrillate the heart of a subject. The voltage at the electrodes is measured during the application of a truncated exponential waveform signal and a time constant $t_s$ is calculated from the rate of change of the voltage at the electrodes. This time constant can then be used in conjunction with a model time constant $t_m$ derived for human cardiac membrane to determine the duration of the pulse which will achieve the desired peak membrane voltage. The duration of the pulse which achieves peak membrane voltage may be obtained by solving the equations described above. The waveform is then interrupted after a pulse of the desired duration has been delivered to the electrodes. The apparatus of FIG. 4 is of particular benefit in carrying out the method of the present invention.

In addition to the method described above, a second truncated exponential waveform signal can be applied to the electrodes to produce a biphasic defibrillating waveform. This second truncated exponential waveform signal is of opposite polarity to the first truncated exponential waveform signal. Optionally, in this alternative method, a second time constant $t_s$ is calculated by measuring the rate of voltage change at the electrodes during application of the second truncated exponential waveform signal. Using the second time constant $t_s$ and the model time constant $t_m$ the duration of the truncated exponential waveform which returns the membrane voltage to the baseline voltage may be determined. The second truncated exponential waveform is then interrupted when this duration is achieved. Optionally a second model time constant $t_m$ for the second exponential waveform may be utilized in calculating the desired duration of the second waveform.

In addition to the methods just described, the model time constant utilized in both the methods employing monophasic defibrillators and the methods employing biphasic defibrillators may be adjusted based upon the model waveform response of the cardiac membrane of a particular subject. The adjustment to the model time constant may, in the case of an implantable defibrillator, occur at the time the defibrillator is implanted in the subject, or, in the case of an external defibrillator at the time the defibrillator is utilized. Furthermore, in the case of an implanted defibrillator the model time constant may be adjusted to compensate for changes in the cardiac membrane of the subject which occur over time. To determine the model time constant the following procedures may be utilized either at the time of implantation, at the time of use or over the life of the implanted defibrillator.

Estimates of $t_m$ may be determined from a pacing strength-duration curve at the time of implantation or periodically by the device. The pacing strength-duration curve for a truncated exponential pacing stimuli can then be fit to the following equation:

$$I_p = \frac{\frac{V_{th}}{c_m}\left(\frac{t_s - t_m}{t_s t_m}\right)}{e^{-\frac{t}{t_s}} - e^{-\frac{t}{t_m}}}$$

where $t_m$ is the model time constant, $c_m$ is the model capacitance, and $t_s$ is the CDW time constant. In the above equation t is the time when $V_{th}$ occurs, the shorter of D or $\ln(t_m/t_s)/(1/t_s - 1/t_m)$ (optimal time). Standard curve fitting techniques can be used to determine $t_m$.

Another embodiment of the present invention involves a method of selecting a cardiac arrhythmia treatment apparatus, such as a cardiac defibrillator, from a set of such apparatus for implantation in a subject. The selection method includes providing a set of implantable cardiac arrythmia treatment apparatus, each of which has a different value for the storage capacitor which delivers a waveform signal, which may be, for example, a truncated exponential waveform signal. During implantation of the cardiac defibrillators a set of electrodes is positioned to provide an electric counter-shock, such as that in defibrillation, to the heart of the subject in which the apparatus is to be implanted. The impedance between the electrodes is then measured. This impedance is then combined with the capacitor values of the cardiac arrythmia treatment apparatus to select the apparatus whose capacitance values produces an RC time constant which most efficiently produces the desired waveform in the subject. Preferably, the RC time constant of the apparatus and the electrodes is equal to the model time constant for cardiac membrane. More preferably, the RC time constant is equal to the model time constant for the cardiac membrane of the subject in which the apparatus is to be implanted. The model time constant of the subject may be determined by the methods described above. The selected apparatus is then implanted in the subject.

An additional aspect of the present invention is to provide a set of implantable cardiac arrhythmia treatment apparatus, such as defibrillators, for implantation into a subject. Preferably the set of apparatus is comprised of three or more members, each member having a storage capacitor which differs from the capacitors of the other members of the set. More preferably the storage capacitors of the apparatus differ by 10 microfarads. Most preferably the set of apparatus comprises apparatus having a storage capacitor of from about 50 microfarads to about 150 microfarads.

EXAMPLE

In the past a capacitor discharge waveform (CDW) has been approximated by a square wave of the same duration (D) and with amplitude equal to the average current ($I_{ave}$) of the CDW. In this approximation, as the CDW gets longer, $I_{ave}$ should approach a constant. Defibrillation studies have shown that for short time constant CDW's, peak current and not $I_{ave}$ becomes constant as the CDW becomes longer. Thus, as D in the denominator of the $I_{ave}$ calculation increases, $I_{ave}$ continues to decrease and does not approach a constant. Using the above equations the threshold-duration curves for CDW's with $t_s$=4, 7, 10 and 15 milliseconds in six dogs. D was 2, 4, 6, 8 and 10 milliseconds. The data was fit to the standard strength-duration relationship: $I_{ave}$=rheo/(1−$e^{-0.693D/t}$), and to the model relationship discussed above. Chronaxie was 2.01±0.38 ms (95% confidence interval).

Rheobase was 5.99±0.53 A. The correlation coefficient for the strength-duration relationship was 0.90. The time constant $t_m$ was 2.64±0.38 ms. $V_{th}/C_m$ was 14.09±1.23 A. The correlation coefficient for our model was 0.97. This model predicts that the optimal D for a CDW is given by the optimal time. For durations longer than D, V no longer increases and so any energy delivered after this time does not contribute to defibrillation.

The foregoing is illustrative of the present invention, and is not to be construed as limiting thereof. The invention is defined by the following claims, with equivalents of the claims to be included therein.

That which is claimed is:

1. A cardiac arrythmia treatment apparatus, comprising:
   (a) shock means for delivering a waveform signal to a pair of electrodes;
   (b) detecting means for detecting an electrical characteristic of said pair of electrodes during delivery of said waveform signal wherein said electrical characteristic is selected from the group consisting of the voltage across said electrodes and the current through at least one of said electrodes;
   (c) time constant calculating means for determining a waveform time constant ($t_s$) from said electrical characteristic;
   (d) storage means for storing a model time constant ($t_m$);
   (e) membrane voltage calculating means for determining when a peak membrane voltage is reached from said waveform time constant and said model time constant; and
   (f) switch means for interrupting said waveform signal when said peak membrane voltage is reached.

2. A cardiac arrythmia treatment apparatus according to claim 1, wherein said apparatus is a biphasic apparatus, said waveform signal is a first waveform signal, and said apparatus further comprising reverse polarity shock means for delivering a second waveform signal after said first waveform signal, with said second waveform signal having a polarity opposite that of said first waveform signal.

3. A cardiac arrythmia treatment apparatus according to claim 2 wherein said first and second waveform signals are truncated exponential waveform signals.

4. A cardiac arrythmia treatment apparatus according to claim 1, wherein said apparatus is a biphasic apparatus, said waveform signal is a second waveform signal, and said apparatus further comprising reverse polarity shock means for delivering a first waveform signal prior to said second waveform signal such that the polarity of said first waveform signal is opposite that of the second waveform signal.

5. A cardiac arrythmia treatment apparatus according to claim 1, wherein:
   said apparatus is a biphasic apparatus,
   said waveform signal is a first waveform signal,
   said apparatus further comprises reverse polarity shock means for delivering a second waveform signal after said first waveform signal, said second waveform signal having polarity opposite that of said first waveform signal;
   said detecting means detects an electrical characteristic of said pair of electrodes during delivery of said second waveform signal wherein said electrical characteristic is selected from the group consisting of the voltage across said electrodes and the current through at least one of said electrodes;
   said time constant calculating means determines a waveform time constant ($t_s$) from said voltage during said second waveform signal;
   said membrane voltage calculating means determines when the membrane baseline voltage is reached from said second waveform time constant and said model time constant; and
   said switch means interrupts said second waveform signal when said membrane baseline voltage is reached.

6. A cardiac arrythmia treatment apparatus according to claim 5, wherein said apparatus further comprises second storage means for storing a second model time constant ($t_m$), and said membrane voltage calculating means determines when the baseline membrane voltage is reached from said second waveform time constant and said second model time constant.

7. A cardiac arrythmia treatment apparatus according to claim 5 wherein said first and second waveform signals are truncated exponential waveform signals.

8. A cardiac arrythmia treatment apparatus according to claim 1 wherein said waveform signal is a truncated exponential waveform signal.

9. A cardiac arrythmia treatment apparatus according to claim 1, further comprising a pair of electrodes connected to said shock means.

10. A cardiac arrythmia treatment apparatus according to claim 1, further comprising adjusting means operably connected to said storage means for altering said model time constant ($t_m$).

11. A cardiac arrythmia treatment apparatus according to claim 1, wherein said apparatus is an implantable apparatus.

12. A cardiac arrythmia treatment apparatus according to claim 1, wherein said apparatus is an external defibrillation apparatus.

13. A cardiac arrythmia treatment method, comprising:
   delivering a waveform signal to a pair of electrodes, said electrodes positioned for defibrillating the heart of a subject;
   detecting an electrical characteristic of said pair of electrodes during delivery of the waveform signal wherein the electrical characteristic is selected from the group consisting of the voltage across the electrodes and the current through at least one of the electrodes;
   determining a first waveform time constant ($t_s$) from the detected electrical characteristic;
   providing a first model time constant ($t_m$) for a model response to the waveform;
   determining when a peak membrane voltage is reached from the waveform time constant and the model time constant; and then
   interrupting the waveform signal when the peak membrane voltage is reached.

14. The method of cardiac arrythmia treatment of claim 13, further comprising the step of delivering a second waveform signal of opposite polarity to the first waveform signal to said pair of electrodes.

15. The method of cardiac arrythmia treatment of claim 14, further comprising the steps of:
   detecting an electrical characteristic of said pair of electrodes during delivery of the second waveform signal wherein the electrical characteristic is selected from the group consisting of the voltage across the electrodes and the current through at least one of the electrodes;
   determining a waveform time constant ($t_s$) from the electrical characteristic during the second waveform signal;
   calculating when the membrane baseline voltage is reached from the second waveform time constant and the model time constant; and interrupting the second waveform signal when the membrane baseline voltage is reached.

16. The method of cardiac arrythmia treatment of claim 15, said method further comprising the steps of:

providing a second model time constant ($t_m$); and wherein said calculating step comprises calculating when the baseline membrane voltage is reached from the second waveform time constant and the second model time constant.

17. The method of cardiac arrythmia treatment of claim 15 wherein the first waveform signal and the second waveform signal are truncated exponential waveform signals.

18. The method of cardiac arrythmia treatment of claim 14 wherein the waveform signal and the second waveform signal are truncated exponential waveform signals.

19. The method of cardiac arrythmia treatment of claim 13, said method further comprising the step of adjusting the model time constant ($t_m$).

20. The method of cardiac arrythmia treatment of claim 13 wherein the waveform signal is a truncated exponential waveform signal.

21. A method of selecting a cardiac arrythmia treatment apparatus for implantation in a subject, comprising:

providing a set of implantable cardiac arrythmia treatment apparatus which deliver a waveform signal, each member of the set having a storage capacitor for delivering the waveform signal, and wherein each member of the set has a storage capacitor with a fixed capacitance different from the other members of the set;

implanting a pair of electrodes in a subject, with the electrodes positioned for applying an electric counter-shock to the heart of the subject; then measuring the impedance across the pair of electrodes after implantation; then selecting a cardiac arrythmia treatment apparatus from the set of cardiac arrythmia treatment apparatus based on the impedance and the storage capacitance of the cardiac arrythmia treatment apparatus; and then implanting the selected cardiac arrythmia treatment apparatus in the subject.

22. The method of selecting a cardiac arrythmia treatment apparatus of claim 21 wherein said selecting step comprises selecting the cardiac arrythmia treatment apparatus having an RC time constant which matches the model time constant of cardiac membrane.

23. The method of selecting a cardiac arrythmia treatment apparatus of claim 21 wherein said selecting step further comprises the steps of:

measuring the model time constant of the cardiac membrane of the subject; and then selecting the cardiac arrythmia treatment apparatus having an RC time constant which matches the model time constant of the cardiac membrane of the subject.

24. The method of selecting a cardiac arrythmia treatment apparatus of claim 21 wherein said measuring step comprises performing a strength duration analysis of the subject.

25. A method of determining the optimum duration of an electric pulse for electric counter-shock cardiac arrythmia treatment comprising:

convolving the waveform of an electric pulse counter-shock signal with the impulse response of a parallel RC circuit having a model time constant to approximate the response of a heart; then determining the peak response time of the waveform from the convolved waveform.

26. The method of claim 25 further comprising the step of generating an electric counter-shock pulse having a duration of the determined peak response time.

27. A method of delivering an electric counter-shock pulse to a subject comprising:

convolving the waveform of an electric pulse counter-shock signal with the impulse response of a parallel RC circuit having a model time constant to approximate the response of a heart;

determining the peak response time of the waveform from the convolved waveform; and delivering said electric counter-shock pulse to a subject.

28. The method of claim 27 further comprising the step of generating an electric counter-shock pulse having a duration of the determined peak response time.

* * * * *